(12) United States Patent
Sklar

(10) Patent No.: US 11,324,933 B2
(45) Date of Patent: *May 10, 2022

(54) APPARATUS FOR MINIMALLY-INVASIVE PREVENTION AND TREATMENT OF HYDROCEPHALUS AND METHOD FOR USE OF SAME

(71) Applicant: Frederick H. Sklar, Dallas, TX (US)

(72) Inventor: Frederick H. Sklar, Dallas, TX (US)

(73) Assignee: Frederick H. Sklar, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/510,680

(22) Filed: Oct. 26, 2021

(65) Prior Publication Data

US 2022/0040459 A1 Feb. 10, 2022

Related U.S. Application Data

(63) Continuation of application No. 16/620,189, filed as application No. PCT/US2018/036558 on Jun. 7, 2018, now Pat. No. 11,154,695.

(Continued)

(51) Int. Cl.
*A61M 27/00* (2006.01)
*A61B 5/021* (2006.01)
*A61B 5/00* (2006.01)

(52) U.S. Cl.
CPC ....... *A61M 27/006* (2013.01); *A61B 5/02116* (2013.01); *A61B 5/6803* (2013.01);
(Continued)

(58) Field of Classification Search
CPC .............. A61M 27/006; A61M 27/002; A61M 2205/3306; A61M 2205/3317;
(Continued)

(56) References Cited

U.S. PATENT DOCUMENTS 4,995,401 A 2/1991 Bunegin et al.
6,283,934 B1 9/2001 Borgesen
(Continued)

OTHER PUBLICATIONS

International Searching Authority, PCT/US18/36558 Notification of Transmittal of the International Search Report and the Written Opinion of the International Searching Authority, or the Declaration, dated Aug. 31, 2018, ISA/US, Alexandria, Virginia.

*Primary Examiner* — Philip R Wiest
(74) *Attorney, Agent, or Firm* — Scott T. Griggs; Griggs Bergen LLP

(57) ABSTRACT

An apparatus for minimally-invasive, including non-invasive, prevention and/or treatment of hydrocephalus and method for use of the same are disclosed. In one embodiment of the apparatus, a housing is sized for superjacent contact with a skull having a fontanel. Within the housing, a compartment includes a pressure applicator, such as a fluid-filled bladder, under the control of a pressure regulator. The pressure applicator is configured to selectively apply an external pressure to the fontanel. The compartment includes a pressure sensor configured to measure intracranial pulse pressure of the fontanel. Further, in one embodiment, the apparatus can cause pulse pressure modulation by adjusting the intracranial pulse pressure via the pressure applicator. This enables a non-invasive measurement of the pulse pressure and modulation thereof in infants, for example.

20 Claims, 9 Drawing Sheets

Related U.S. Application Data

(60) Provisional application No. 62/516,359, filed on Jun. 7, 2017.

(52) U.S. Cl.
CPC ............... *A61B 2562/0247* (2013.01); *A61M 2205/3306* (2013.01); *A61M 2205/3317* (2013.01); *A61M 2205/3375* (2013.01); *A61M 2205/52* (2013.01); *A61M 2205/587* (2013.01); *A61M 2210/0687* (2013.01); *A61M 2230/30* (2013.01); *A61M 2240/00* (2013.01)

(58) Field of Classification Search
CPC ........ A61M 2205/52; A61M 2205/587; A61M 2210/0687; A61M 2230/30; A61M 2240/00; A61B 5/02116; A61B 5/6803; A61B 2562/0247
See application file for complete search history.

(56) References Cited

U.S. PATENT DOCUMENTS

| | | | |
|---|---|---|---|
| 11,154,695 B2* | 10/2021 | Sklar | A61B 5/02438 |
| 2013/0085400 A1 | 4/2013 | Oliveira et al. | |
| 2015/0005800 A1* | 1/2015 | Anile | A61M 27/006 |
| | | | 606/192 |
| 2015/0268673 A1 | 9/2015 | Farzbod et al. | |

* cited by examiner

APPARATUS FOR MINIMALLY-INVASIVE PREVENTION AND TREATMENT OF HYDROCEPHALUS AND METHOD FOR USE OF SAME

PRIORITY STATEMENT & CROSS-REFERENCE TO RELATED APPLICATIONS

This application is a continuation of U.S. patent application Ser. No. 16/620,189 entitled "Apparatus for Minimally-Invasive Prevention and Treatment of Hydrocephalus and Method for Use of Same" filed on Dec. 6, 2019 in the name of Frederick H. Sklar, now U.S. Pat. No. 11,154,695 issued on Oct. 26, 2021; which is the National Stage of, and therefore, claims the benefit of the Jun. 7, 2018 filing date of international application PCT/US2018/036558, which designates the United States, filed in the name of Frederick H. Sklar and entitled "Apparatus for Minimally-Invasive Treatment of Hydrocephalus and Method for Use of Same"; which claims priority from U.S. Patent Application Ser. No. 62/516,359 entitled "Apparatus for Minimally-Invasive Treatment of Hydrocephalus and Method for Use of Same" filed on Jun. 7, 2017 in the name of Frederick H. Sklar; all of which are hereby incorporated by reference, in entirety, for all purposes.

TECHNICAL FIELD OF THE INVENTION

This invention relates, in general, to the treatment of hydrocephalus and, in particular, to an apparatus for the minimally-invasive, including non-invasive, prevention and/or treatment of hydrocephalus in premature infants, term infants, and other individuals and method for use of the same.

BACKGROUND OF THE INVENTION

Cerebrospinal fluid (CSF) is made within the ventricles of the brain and percolates through the ventricular system in response to brain pulsations. In normal circumstances, CSF exits in the fourth ventricle and circulates over the surface of the brain and around the spinal cord to be absorbed into the venous system. Hydrocephalus is a disease that is assumed to occur when the absorption mechanisms are not in equilibrium with the rate of CSF production. The disease is characterized by enlargement of the cerebral ventricles, abnormally high intracranial pressure (ICP), and large heads in children. In addition, the elderly can develop so-called normal pressure hydrocephalus (NPH). In addition, approximately 22% of premature infants have germinal matrix hemorrhages, commonly referred to as intraventricular hemorrhages (IVH), and many of these babies develop post-hemorrhagic hydrocephalus. Approximately 50% of babies with IVH develop ventricular enlargement, and half of these clearly have progressive hydrocephalus, frequently requiring neurosurgical treatment. The other half are said to have so-called arrested hydrocephalus, although slowly-progressive, active hydrocephalus remains a possibility.

The prevailing treatment options for hydrocephalus are limited. Some patients develop obstructive hydrocephalus as a result of an intracranial tumor distorting or blocking CSF pathways. Treating the tumor frequently corrects the hydrocephalus problem. Approximately 90% of children with posterior fossa tumors and hydrocephalus do not require permanent shunts for their hydrocephalus once the tumor has been removed. Some selected patients with obstructive hydrocephalus such as aqueductal stenosis can benefit from endoscopic third ventriculostomy (ETV). However, the majority of patients with hydrocephalus require shunt surgery.

This surgical treatment involves the implantation of a Silastic® device—a cerebrospinal fluid shunt (CSF shunt)—to divert fluid from the brain ventricles to another body compartment, where the CSF can be absorbed into the venous system. Shunt surgery has had a tremendous positive impact on neurosurgery and represents a significant clinical advancement of the 20th century. Shunt surgery has become the mainstay treatment of hydrocephalus. There are numerous valves and shunt systems available in the marketplace. Some utilize relatively simplistic pressure differential valves; some are regulated by flow; and some are programmable. There are reservoirs, antibiotic treated components, and anti-siphon devices. Shunts can malfunction, obstruct, break, or get infected. Thirty percent of shunts fail in the first year after placement. Over-shunting is common, and many patients experience headaches from intracranial hypotension. Some patients can develop subdural hematomas as a result of the ventricular decompression and tearing of bridging veins.

CSF absorption is a sensitive function of ICP; it increases significantly as pressure is increased. Even in communicating hydrocephalus, CSF increases with increasing ICP, although not as much. CSF production is essentially independent of ICP, or may decrease slightly at very high pressures. In other words, there is an absorptive reserve in which absorption exceeds production, and this is maintained even in hydrocephalus.

Ventricular pulsations may be particularly important in the development of hydrocephalus. Augmentation of the ventricular pulse pressure in goats with pulsating balloons synchronized to the cardiac cycle causes hydrocephalus. The pulse pressure in the ventricle with the shunt catheter is smaller than in the other lateral ventricle. Scans show that the shunted ventricle is typically smaller than the other side. Subgaleal shunts divert ventricular CSF into a pocket under the scalp, effectively treating the hydrocephalus, at least temporarily. Subarachnoid hemorrhage patients frequently develop hydrocephalus. Ventricular drainage is frequently used in these patients, and the intracranial pulsations have been noted to gradually increase even though ICP is held constant.

It is possible that shunts work by dampening the ventricular pulse pressure (PP). Diversion of CSF into the peritoneal cavity, pleural cavity, heart, gall bladder, or subgaleal space may be only an epiphenomenon. Further, shunts may be effective in treating hydrocephalus only because a small volume of CSF is displaced out of the ventricle with every heartbeat, therefore reducing the intraventricular pulse pressure. Shunts may work simply because they are shock absorbers. Numerous mathematical models of the CSF system have been suggested and some more recent studies draw parallels with electrical circuitry suggest that increases in ventricular pulsations, indeed, cause hydrocephalus.

In newborns with an open fontanel, the intracranial pulsations can be monitored and modulated through the fontanel without invasive surgical implantation of an intracranial device. Accordingly, hydrocephalus can likely be treated in these infants without surgery, at least until the fontanel begins to close. In premature infants with intraventricular hemorrhage (IVH), who are at risk for developing post-hemorrhagic hydrocephalus, not only can hydrocephalus be treated with PP modulation in infants who already have the disease, but it can also be prevented with PP modulation that offsets the gradual increases in mean intracranial PP during the days, weeks, or months subsequent to the IVH. Advances in medical science are needed to treat hydrocephalus, particularly in premature infants.

SUMMARY OF THE INVENTION

It would be advantageous to achieve an advanced, non-surgical device that can prevent and treat post-hemorrhagic hydrocephalus in premature infants, as well as treating other forms of hydrocephalus in babies with an open fontanel. It would also be desirable to enable a medical-based solution that mitigates the enlargement of the cerebral ventricles and abnormally high intracranial pressure (ICP), particularly in premature infants. To better address one or more of these concerns, an apparatus is disclosed for the minimally-invasive, including non-invasive, prevention and treatment of hydrocephalus, in premature infants and others and a method for use of the same. In one implementation, the apparatus modulates intracranial pulse pressure (PP) though the fontanels of premature and term infants.

The PP is the arithmetic difference between the peak pressure in systole and the lowest pressure in diastole. The terms "pulse pressure modulation" are being used to describe a therapeutic technique that measures the intracranial pulse pressure and adjusts it by either reducing or increasing the intracranial PP according the clinical situation. Moreover, a device that allows non-invasive measurement of ICP and intracranial PP in babies with open fontanels would be a useful clinical tool, not only for patients in neonatal intensive care units but also older infants with open fontanels and ICP issues.

In one embodiment of the apparatus, a housing is sized for superjacent contact on a premature infant skull having a fontanel. Within the housing, a compartment includes a pressure applicator, such as a fluid-filled bladder, under the control of a pressure regulator. The pressure applicator is configured to selectively apply an external pressure to the fontanel. The compartment includes a pressure sensor configured to, in one embodiment, measure displacement, including pulsations, of the fontanel. The apparatus determines intracranial PP. Further, in one embodiment, the apparatus can cause pulse pressure modulation by adjusting the intracranial pulse pressure via the pressure applicator. This enables a non-invasive measurement of the pulse pressure and modulation thereof in infants, for example. More specifically, in one embodiment, to reduce intracranial PP in order to prevent or treat hydrocephalus after IVH, the apparatus monitors pulsations of the fontanel and responds to intracranial pressure increases during systole with relaxation of the pressure applicator, which may be a fluid-filled bladder within a closed component with a ventral opening, positioned on the fontanel thereby reducing the systolic pressure. During diastole, the fluid-filled bladder is gently refilled, thereby increasing the diastolic pressure. The cumulative effect of this cyclical process would work to decrease the intracranial PP. The mean ICP will likely not change, or it may decrease. In this setting, the apparatus may include a solenoid pump and controller software to modulate the intracranial PP.

Clinical conditions may exist in which augmentation of the intracranial PP may be desirable, such as to increase cerebral blood flow (CBF). In such a setting, the apparatus may function to withdraw fluid from the bladder during diastole and reinject this volume back into the bladder during systole. The cumulative result of this process will increase intracranial PP. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1:
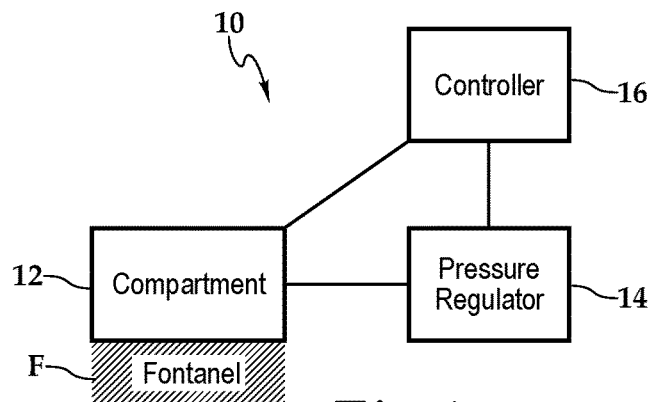
FIG. 1 is a functional block diagram depicting one embodiment of an apparatus for the minimally-invasive, including non-invasive, prevention and treatment of hydrocephalus in premature infants, term infants, and other individuals, according to the teachings presented herein.

Referring initially to FIG. 1, therein is depicted one embodiment of an apparatus 10 for minimally-invasive, including non-invasive, prevention and treatment of hydrocephalus in premature infants, term infants, and other individuals. The apparatus 10 is sized for superjacent contact on a premature infant skull, for example, having a fontanel F. The apparatus 10 includes a compartment 12, a pressure regulator 14, and a controller 16. The compartment 12 may be selectively adjustable or fixed and configured to selectively apply pressure via pressure applicator such as a bladder, for example, under control of the pressure regulator 14, to the fontanel F. The pressure applicator may operate under hydraulic actuation, mechanical actuation, or a combination thereof. The compartment may then measure intracranial pulse pressure (PP) at the fontanel F and, if clinically applicable, pulse pressure modulate. The controller 16 is interconnected communicatively with each of the compartment 12 and the pressure regulator 14.

Figure 2:
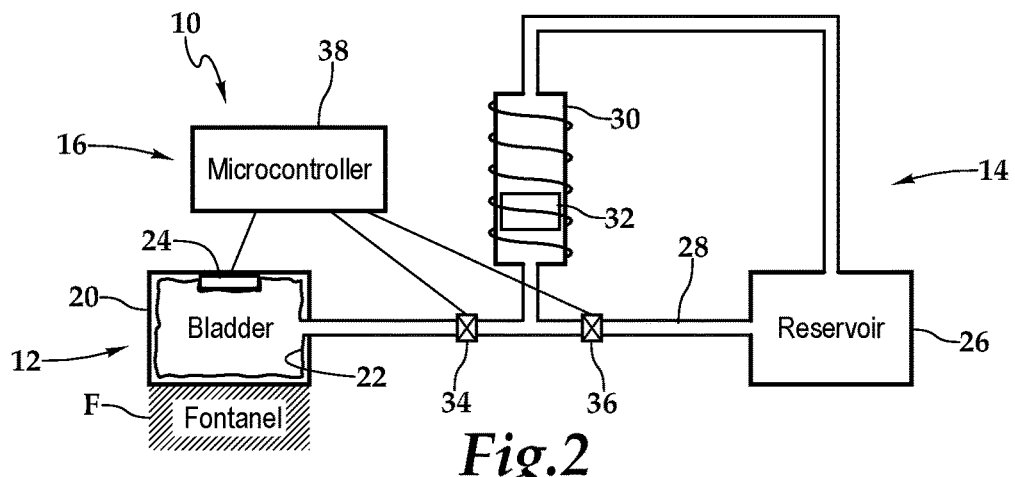
FIG. 2 is a functional block diagram depicting another embodiment of an apparatus for the minimally, invasive, including non-invasive, measurement of ICP and modulation of intracranial PP as a prevention and treatment of hydrocephalus in premature infants, term infants, and other individuals, according to the teachings presented herein.
Figure 3:
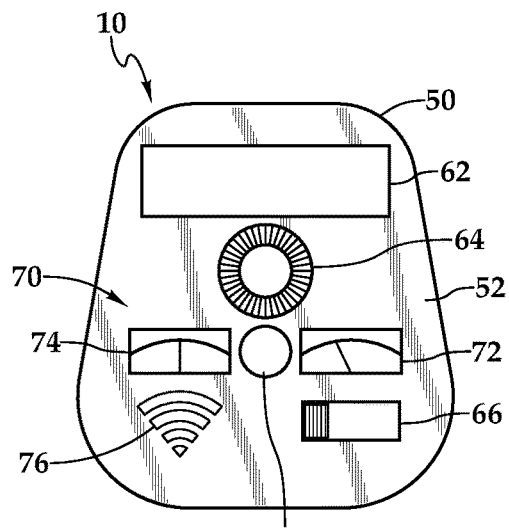
FIG. 3 is a top plan view depicting one operational embodiment of the apparatus of FIG. 1 and FIG. 2.
Figure 4:
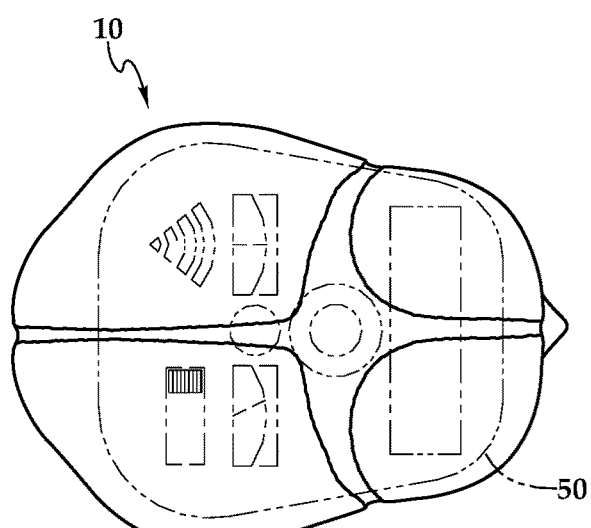
FIG. 4 is a top plan view depicting the operational embodiment of the apparatus of FIG. 3 in ghost to demonstrate a placement of the apparatus on the skull of a premature infant.
Figure 5:
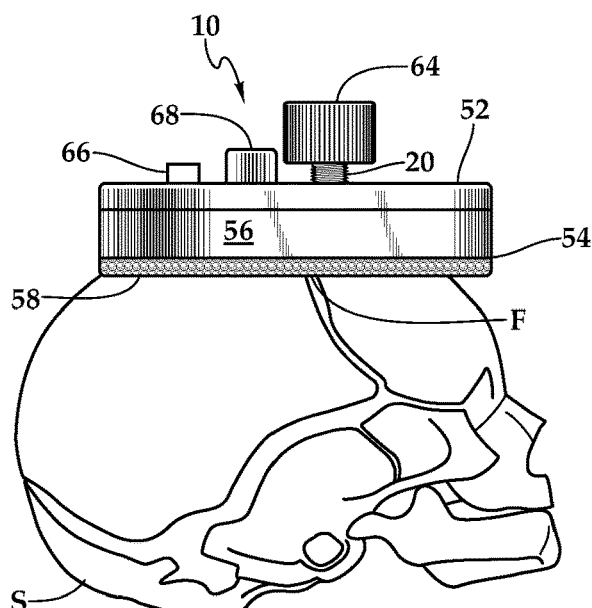
FIG. 5 is a side elevation view depicting the operational embodiment of the apparatus of FIG. 3 on the skull of the premature infant.
Figure 6:
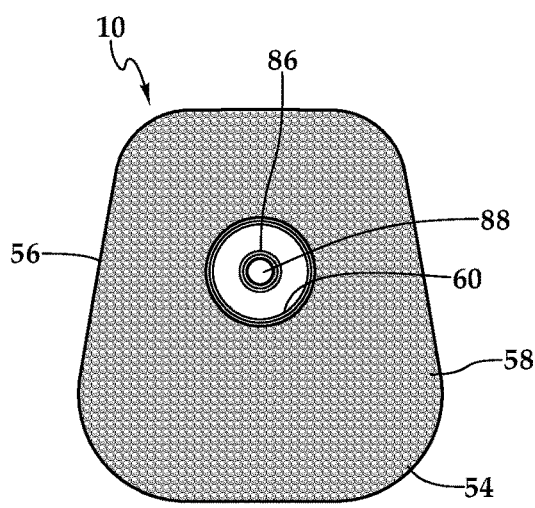
FIG. 6 is a bottom plan view depicting the operational embodiment of the apparatus of FIG. 3.
Figure 7:
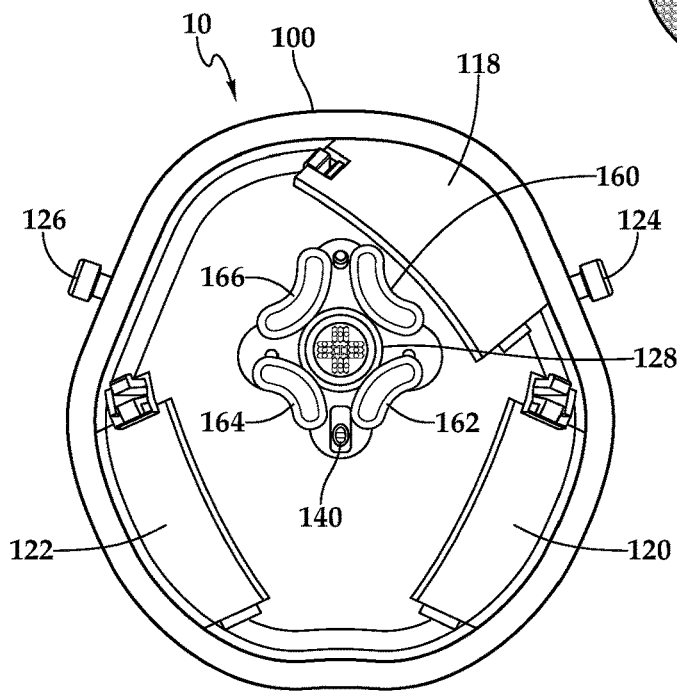
FIG. 7 is a top plan view depicting another operational embodiment of the apparatus of FIG. 1 and FIG. 2.
Figure 8:
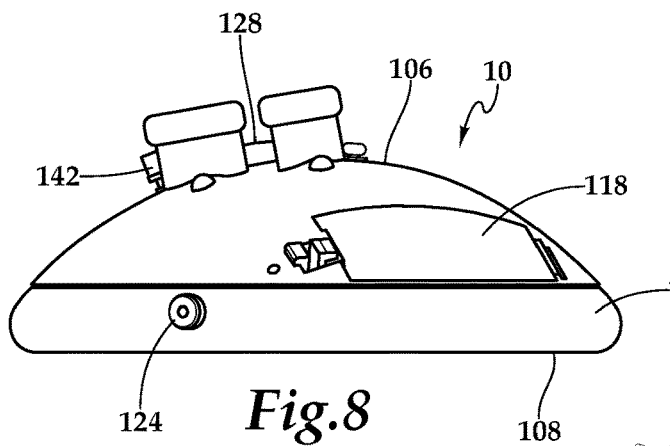
FIG. 8 is a side elevation view depicting another operational embodiment of the apparatus of FIG. 7.
Figure 9:
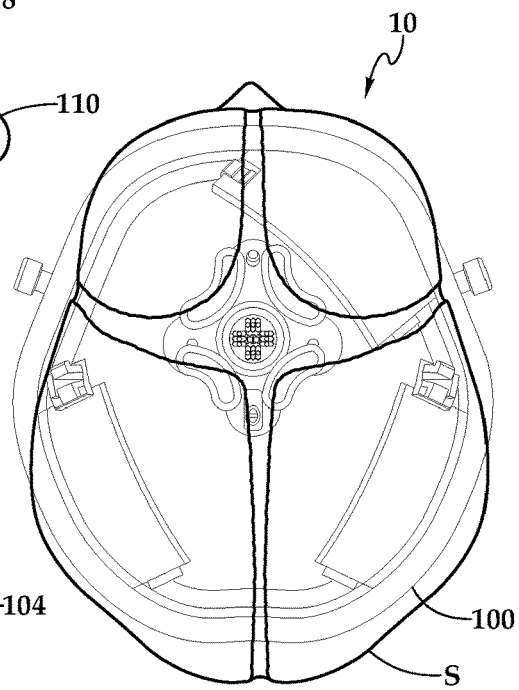
FIG. 9 is a top plan view depicting the operational embodiment of the apparatus of FIG. 7 in ghost to demonstrate a placement of the apparatus on the skull of a premature infant.
Figure 10:
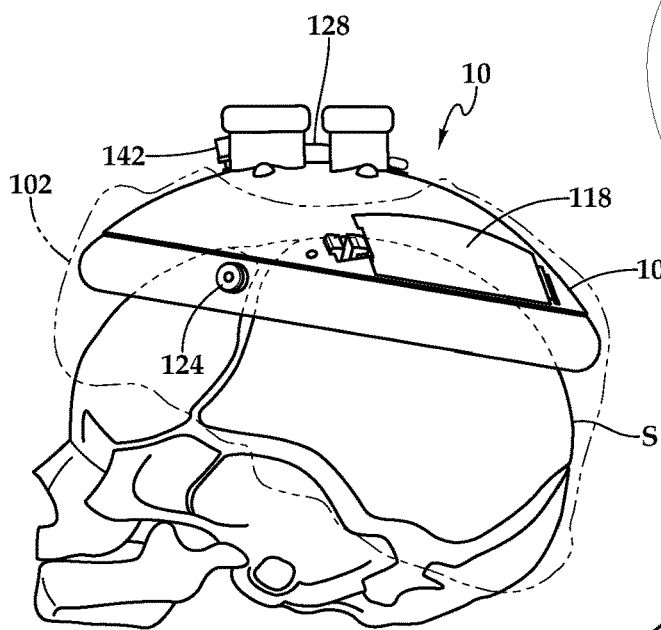
FIG. 10 is a side elevation view depicting the operational embodiment of the apparatus of FIG. 7 on the skull of the premature infant, held in place with a custom knit cap.
Figure 11:
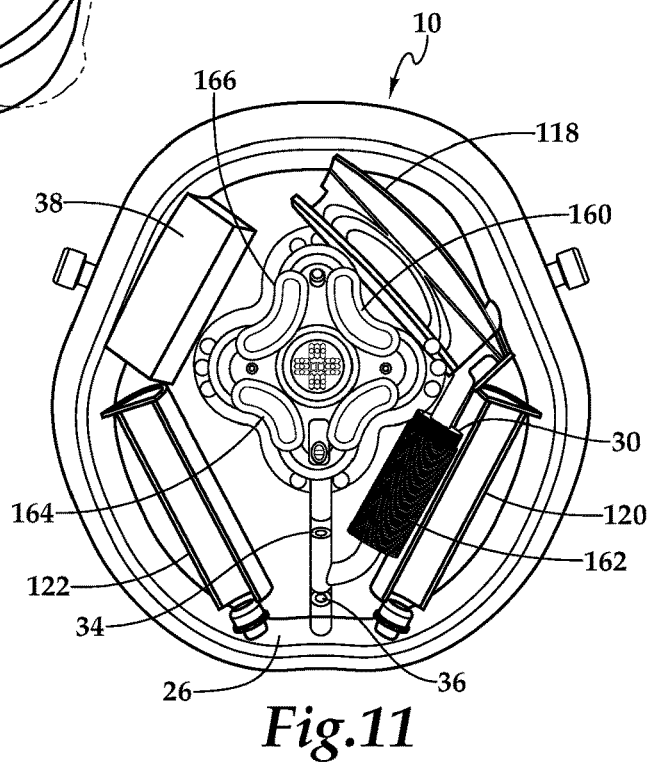
FIG. 11 is a top plan interior view depicting the operational embodiment of the apparatus of FIG. 7 with components selectively removed to reveal the interior.
Figure 12:
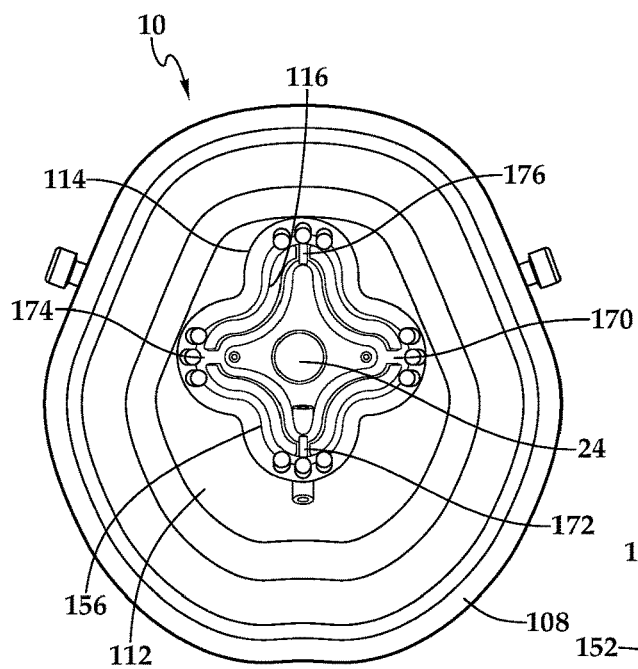
FIG. 12 is a bottom plan view depicting the operational embodiment of the apparatus of FIG. 7.
Figure 13:
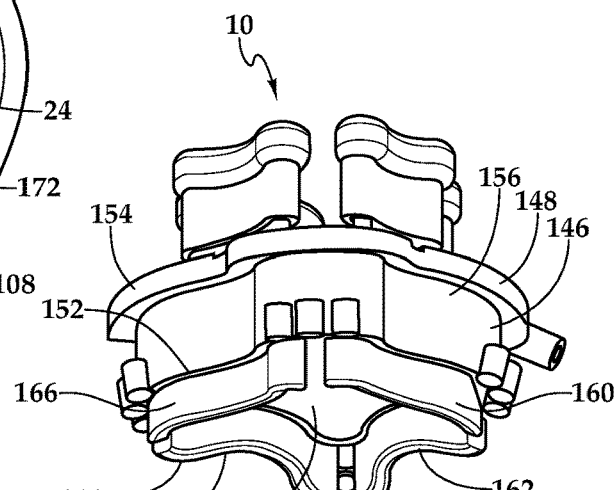
FIG. 13 is a side perspective view depicting one embodiment of a central compartment, which forms a portion of the apparatus of FIG. 7.
Figure 14:
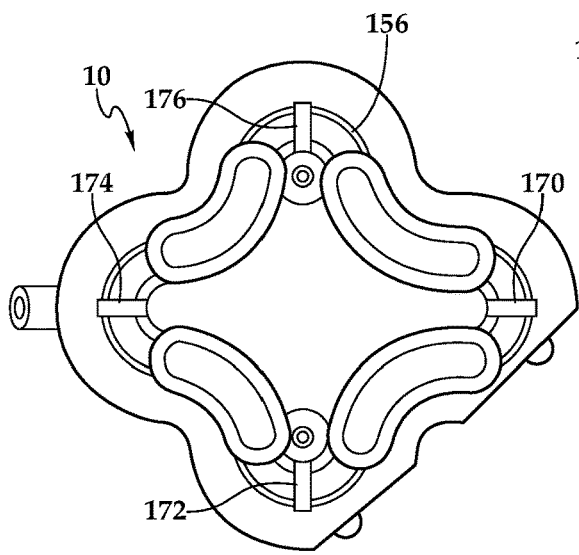
FIG. 14 is a top plan view depicting the central compartment of FIG. 13.
Figure 15:
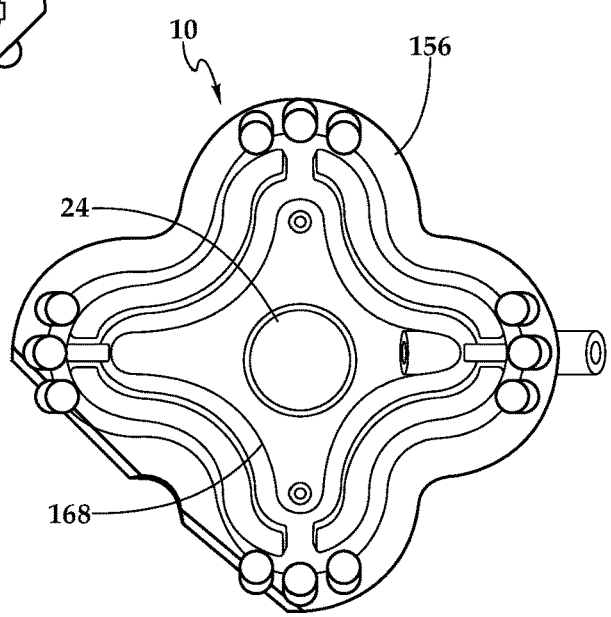
FIG. 15 is a bottom plan view depicting the central compartment of FIG. 13.
Figure 16:
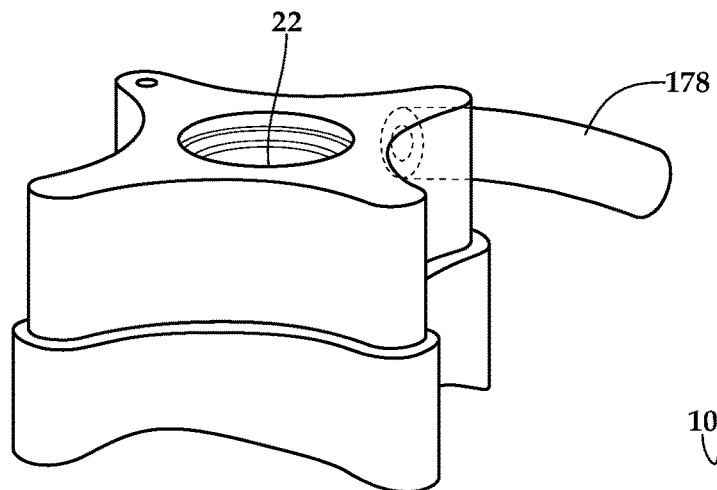
FIG. 16 is a side perspective view of one embodiment of a bladder, which forms a portion of the apparatus of FIG. 7.

FIG. 2 depicts another embodiment of the apparatus 10 for minimally invasive, including non-invasive, monitoring of intracranial pressure (ICP) as well as intracranial PP, in addition to prevention and treatment of hydrocephalus in premature infants with intraventricular hemorrhage (IVH) or in other babies with open fontanels who have hydrocephalus or intracranial hypertension. As shown, the compartment 12 may be a central compartment 20 securing a pressure applicator depicted as a bladder 22, which may be a form of a sealed vessel, and a pressure sensor depicted as a disk pressure transducer 24 therein. The pressure regulator includes a fluid reservoir 26 fluidly coupled to the bladder 22 by tubing 28 with a solenoid pump 30 and a magnet piston 32 as well as valves 34, 36 controlling the fluid flow between the bladder 22 at the compartment 12 and the fluid reservoir 26. The controller 16 is depicted as a microcontroller 38 and, as shown, is interconnected communicatively with each of the compartment 12 and the pressure regulator 14.

The disk pressure transducer 24 may measure displacement, including pulsations, of the fontanel F. The apparatus 10 may determine intracranial PP in response to the displacement of the fontanel F. In one embodiment, to reduce intracranial PP in order to prevent or treat hydrocephalus after IVH, the apparatus 10 monitors pulsations of the fontanel F and responds to intracranial pressure increases during systole with relaxation of the fluid-filled bladder 22, positioned on the fontanel F thereby reducing the systolic pressure. During diastole, the fluid-filled bladder 22 is gently refilled, thereby increasing the diastolic pressure. The cumulative effect of this cyclical process would work to decrease the intracranial PP. The mean ICP will likely not change, or it may decrease.

Clinical conditions may exist in which augmentation of the intracranial PP may be desirable, such as to increase cerebral blood flow (CBF). In such a setting, the apparatus 10 may function to withdraw fluid from the bladder 22 during diastole and reinject this volume back into the bladder 22 during systole. The cumulative result of this process will increase intracranial PP.

Referring now to FIG. 3 through FIG. 6, the apparatus 10 includes a housing 50 sized for superjacent contact on a premature infant skull S having the fontanel F. It should be appreciated that although a premature infant skull S is depicted for illustrative purposes, the apparatus 10 may be utilized with premature infants, term infants, and other individuals. The housing 50 is configured to fit within a cap formed by a tube of stretchable material closed at one end; the other end of the tube being dimensioned for a close fit about the premature infant skull. As shown, the housing includes an upper plate 52, a lower plate 54, and a vertical sidewall 56 therebetween. A gel pad 58 located on the lower plate 54 contacts the premature infant skull S. An opening 60 through the lower plate 54 and the gel pad 58 is sized for the fontanel F. As previously alluded, the housing 50 secures the compartment 12, the pressure regulator 14, and the controller 16 therein.

A battery compartment door 62 is positioned in the upper plate 52 to provide access to a battery compartment. A locking knob 64 extends from the compartment 12, which may include a central compartment 20, and provides for the placement of the compartment 12, including extension from the lower plate 54 of the housing 50 and retraction into the lower plate 54 of the housing 50. As previously mentioned, in other embodiments, the compartment 12 and the central compartment may be static or utilize a different mechanism for determining and maintaining position. A power switch 66, which is located in the upper plate 52, enables a user to turn the apparatus 10 ON and OFF. A position user interface 68, which is also located in the upper plate 52, enables a user to mark the position of the apparatus relative to the premature infant skull S and the fontanel F. Various displays 70 are positioned in the upper plate 52. In the illustrated embodiment, the displays 70 include a position monitor 72, an ammeter display 74, and a wireless signal strength indicator 76.

The compartment 12 may traverse the housing 50 from the upper plate 52 to the lower plate 54. The locking knob 64 is coupled to the central compartment such that the locking knob 64 is superjacent to the upper plate 52. The locking knob 64 is configured to selectively adjust the compartment 12 to extend from the opening 60 and to retract within the opening 60. The central compartment 20 may house a pressure applicator 88 and a pressure sensor 90. It should be appreciated that although a particular device configuration with respect to inputs and outputs is shown with respect to the apparatus 10, other device configurations are within the teachings presented herein and any device configuration selected will depend on multiple factors.

Referring now to FIG. 8 through FIG. 22, in another embodiment, the apparatus 10 includes a housing 100 sized for superjacent contact on a premature infant, for example, skull S having the fontanel F. The housing 100 is configured to fit within a stretch knit cap 102, tailored for a close fit about the skull S of the premature infant or other individual. The stretch knit cap 102 attaches to a superior-lateral convexity surface 104 of housing 100. As shown, the housing 100 also includes a contoured upper plate 106, a similarly curved lower plate 108, and an intervening curved sidewall 110 that contains a fluid reservoir 26 therein, which may encircle the perimeter of the apparatus 10. A gel pad 112, located on the inferior surface of the lower plate 108, contacts the premature infant skull S. The gel pad includes an opening 114 therethrough. The gel pad 112 may have a slightly adhesive surface which helps to keep the apparatus from becoming dislodged, once it has been correctly positioned. A clover leaf-shaped opening 116 through lower plate 108 and the opening 114 through the gel pad 112 are positioned and sized to approximate the fontanel F. As previously alluded, the housing 100 contains a central compartment 20, which may open inferiorly. Within the central compartment 20 is the inflatable fluid-filled bladder 22 and the disk pressure transducer 24. Adjacent to the central compartment 20 is the solenoid pump 30, valve 34, valve 36, and the microcontroller 38 therein. Although in FIGS. 8 through 22, the fluid-filled bladder 22 is described with reference to hydraulic actuation, the actuation may occur mechanically as will be discussed hereinbelow.

Three battery compartment doors 118, 120, 122 are positioned in the upper plate 106 to provide access to the respective battery compartments. It should be appreciated that the power requirements of the apparatus 10 may vary and the type and number of batteries or other power source will depend on various engineering factors and the number of battery compartment doors may differ than the illustrated embodiment. Water or another fluid is introduced into the fluid reservoir 26 through one of two ports 124, 126 while the unused port 124, 126 allows the extraction of air from the internal plumbing system.

In one operational embodiment, prior to placing the device 10 on an individual's head, the cranial sutures adjacent to the fontanel F are marked by the care provider with ink containing metallic particles. Approximately 2-3 cm of each suture adjacent to the fontanel F are marked, including the superior metopic, rostral sagittal, and both coronal sutures.

In one embodiment, the care provider then applies the apparatus 10 over the fontanel F, adjusting its position until the metopic-sagittal and the bicoronal axes are aligned according to a position detector 128 on the upper plate 106.

Figure 17:
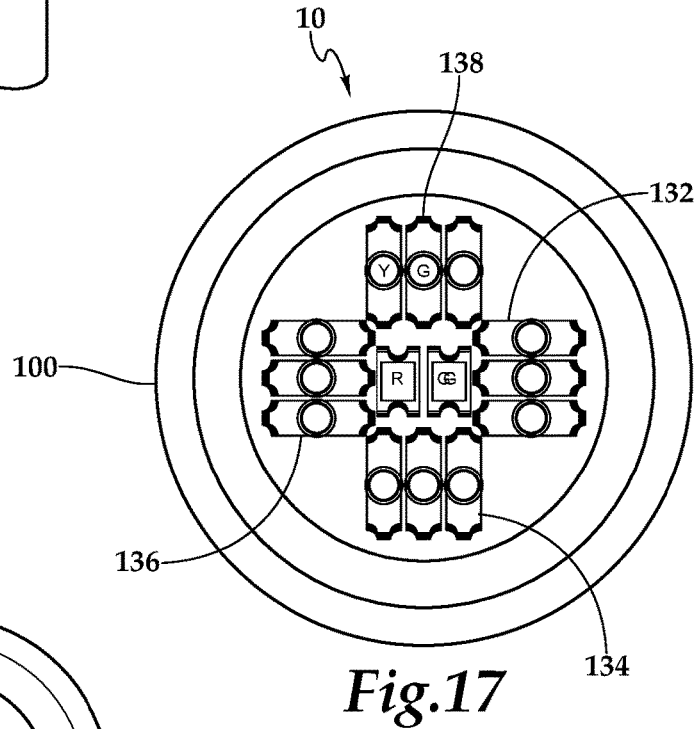
FIG. 17 is a top plan view of one embodiment of a position detector, which forms a portion of the apparatus of FIG. 7.
Figure 18:
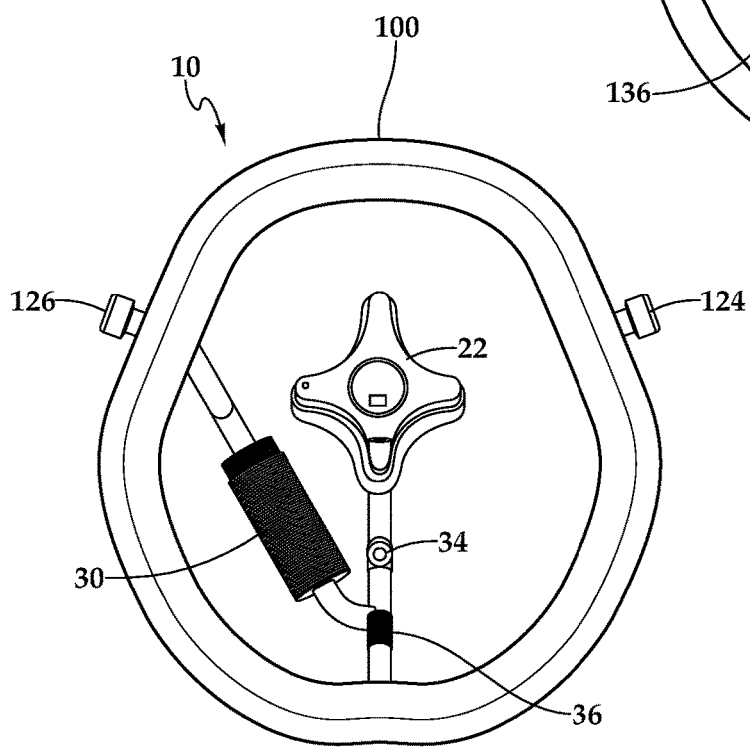
FIG. 18 is a top plan view of one embodiment of fluid power components, which form a portion of the apparatus of FIG. 7.
Figure 19:
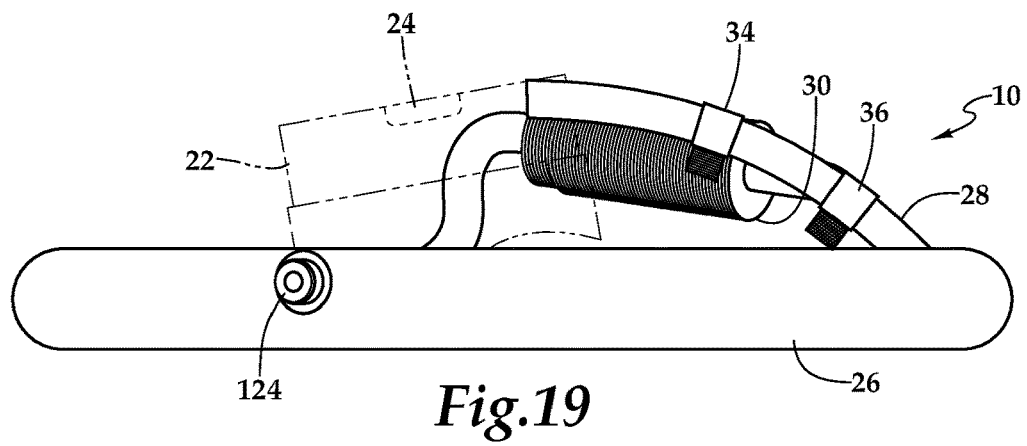
FIG. 19 is a side elevation view of the fluid power components of FIG. 18.
Figure 20:
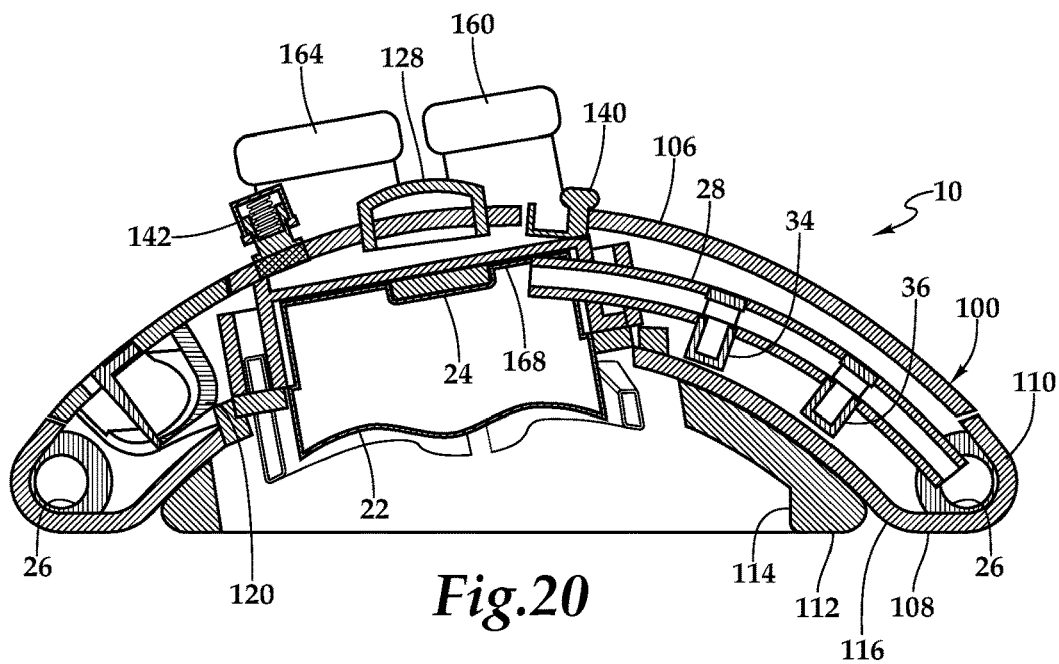
FIG. 20 is a longitudinal cross-sectional view depicting the operational embodiment of the apparatus of FIG. 7.
Figure 21:
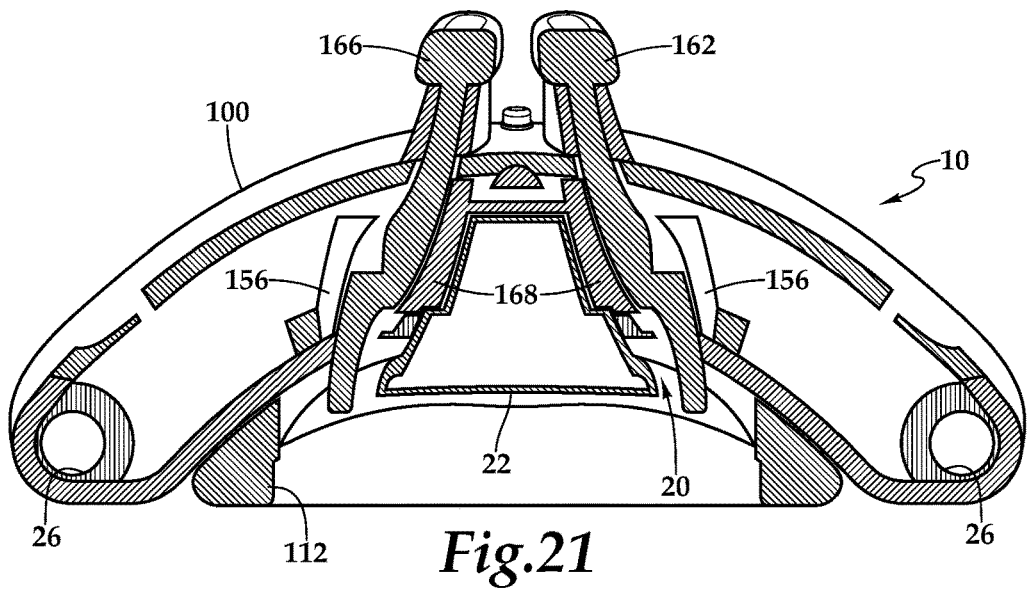
FIG. 21 is a transverse cross-sectional view depicting the operational embodiment of the apparatus of FIG. 7.

As best illustrated in FIG. 17, the position detector 128 has four groups of three LED lights that are arranged to indicate the corners of the fontanel F: front and back, and right and left, respectively. In each group, a central green LED is positioned between two yellow LEDs. Each of the twelve LEDs 130 correspond to a specific capacitance position sensor 132, 134, 136, 138 located within the lower plate 108 adjacent to opening 114 and the central compartment 20. In one embodiment, the goal is to position the center capacitance sensor of each group 132, 134, 136, 138 over its respective cranial suture. The remaining two sensors in each group 132, 134, 136, 138 are positioned closely adjacent to the center sensor (one on each side of the central sensor). For the coronal sutures, the two groups of three capacitance sensors each form a gentle arc positioned approximately in a sagittal plane. For the metopic and sagittal sutures, the two groups of three sensors are also arranged in arcs generally oriented in the coronal plane. When the apparatus 10 is placed onto the head and an ON-OFF switch 140 is activated, the microcontroller 38 measures the electrical signal from each sensor of each group 132, 134, 136, 138, identifying the relative proximity to the underlying suture marked with metallic ink. The microcontroller 38 accordingly lights that LED in each of the four groups of the LEDs 130 with the highest signal. When the position of the apparatus 10 has been adjusted so that all four of the green center LEDs are lit, a larger, square-shaped green LED in the center of the position detector 128 is lit by the microcontroller 38, and the previously lit adjacent, square-shaped red LED will go off. The care provider then pushes a button 142, just rostral to the position detector 128, to indicate to the microcontroller 38 this baseline positioning of the apparatus 10 over the cranial sutures. Further, the microcontroller 38 activates an alarm system to detect if the apparatus 10 has dislocated from its baseline position. If it has become dislodged, a remote alarm is triggered, so that the apparatus 10 can be repositioned.

Spaced around the curvilinear perimeter of the apparatus 10 may be an EKG lead and an EKG ground, each attached to the ventral surface of the gel pad 112. A second EKG lead may be located on the inside surface of a stretch "sweatband," sized to fit a premature infant's forearm or lower leg above the ankle, for example. The cranial EKG lead and ground may be connected directly to the microcontroller 38, located within the housing 100, and the limb lead communicates wirelessly so that the QRS complex can be recorded by the computer to provide an estimate of the onset of systole. A green LED light on the limb lead housing may indicate that wireless connection has been made with the apparatus and that EKG is being received. A red LED light may indicate when the battery needs to be replaced or recharged. A miniature pulse oximeter may be incorporated into the gel pad interface to monitor the patient's oxygen saturation. In another embodiment, pulse oximetry can alternatively be used to determine cardiac systole.

Inside the housing 100 of the apparatus 10 is the central compartment 20, which may resemble the shape of a four leaf clover. Approximately centered on the fontanel F, the central compartment 20 in one embodiment is comprised of three concentrically oriented clover-leaf structures 144, 146, 148 with respective vertical walls 150, 152, 154 are in close apposition. In addition, the central compartment 20 includes the inflatable bladder 22 and the disk pressure transducer 24. More particularly, a continuous clover-leaf outer wall 156, which is fixed to the upper plate 106 and extends to the lower plate 108, is provided. An intermediate, discontinuous, cover-leaf component 158 includes four separate vertical sliders 160, 162, 164, 166 that may be independently raised or lowered so that each slider 160, 162, 164, 166 is in contact with the underlying scalp.

A clover leaf-shaped inner compartment 168 includes continuous vertical walls and a ceiling. The walls of the inner compartment 168 are rigidly attached to the outer wall 156 of the central compartment 20 by four plastic bridges 170, 172, 174, 176 which appropriately partition the space between the outer and inner walls for the four vertical sliders 160, 162, 164, 166. The vertical sliders 160, 162, 164, 166 extend below the bottom of the inner compartment 168 and can be lowered to touch the scalp. Attached to the under surface of the ceiling of the inner compartment 168 is the disk pressure transducer 24, monitored by microcontroller 38.

The bladder 22 may be an inflatable bladder of Silastic® material, or other elastic material, contoured to fit closely within the space created by the inner compartment 168 within the central compartment 20, the vertical sliders 160, 162, 164, 166, and the scalp. The vertical sliders 160, 162, 164, 166 function to provide a concentric, adjustable, inferior extension of the central compartment 20 down to the scalp, thus creating a closed space for meaningful pressure measurements. The bladder 22 is attached to a hollow tubing 178 which leads to the valve 34, the solenoid pump 30, the valve 36, and the fluid reservoir 26. Additionally, there is a tube 180 that connects without a valve the back end of the solenoid pump 30 with the reservoir 26 to prevent the development of undesirable pressure differentials across the pump plunger when the solenoid pump 30 is infusing or withdrawing fluid.

As shown, in one embodiment, the disk pressure transducer 24 may be attached to the ceiling of the inner compartment 168 to measure the pressure in the space of the central compartment 20 when the bladder 22 has been inflated and clear pressure waveforms are detected by microcontroller 38. The disk pressure transducer 24 may include a sensor belonging to displacement sensors, piezoresistive sensors, capacitive sensors, piezoelectric sensors, ultrasonic sensors, or optical sensors, for example.

In one embodiment, the four vertical sliders 160, 162, 164, 166 are individually lowered by the care provider to make contact with the scalp, regardless of skull asymmetries or irregularities at the cranial vertex. It should be appreciated that in another embodiment more than four vertical sliders may be utilized to provide more accurate contact with the scalp. In the present embodiment, each of the vertical sliders 160, 162, 164, 166 extends up through the upper plate 106 of the apparatus 10 and has a handle so that it can be manually raised away from or lowered down to touch the scalp adjacent to the fontanel F. In another embodiment, each vertical slider 160, 162, 164, 166 is raised or lowered by a micro-electric motor under the control of the microcontroller 38. In both of these embodiments, the inferior edge of each vertical slider 160, 162, 164, 166 is covered with metal foil or another conductive material that will not irritate the scalp to which a small electric current is applied. As each vertical sliding member 160, 162, 164, 166 is lowered to rest onto the scalp, the amperage of the foil is monitored by the microcontroller 38. When the foil contacts the skin, the microcontroller 38 detects a significant change in electrical conductance (amperage) and causes a small green (or other color) LED to light on the upper plate 106 next to the handle of its respective vertical slider 160, 162, 164, 166. When all four vertical sliders 160, 162, 164, 166 are in contact with the scalp, there will be four green (or other color) lights adjacent to the handles of the vertical sliders.

As noted, the inflatable bladder 22 fills the closed space of the central compartment 20, which is created when the vertical sliders are all in contact with the scalp. In one embodiment, the small disc pressure transducer 24 is attached to the inferior surface of the inner compartment 168 ceiling, and pressure recordings are monitored by the microcontroller 38. Initially, the controller 16 inflates bladder 22 by selectively working the valve 34 and the valve 36 to have the solenoid pump 30 infuse fluid from the fluid reservoir 26 into bladder 22 until pulsations with distinct waveforms are detected by microcontroller 38. At this time, the pressure within the central compartment 20 closely approximates both the pressure in bladder 22 and ICP. Accordingly, ICP can then be monitored continuously as long as apparatus 10 is not dislodged from its position on the head. Pressure and other physiologic data can be wirelessly downloaded to a remote monitor.

In one embodiment, to modulate the intracranial pulse pressure by reducing PP in order to treat hydrocephalus, the microcontroller 38 first determines representative measurements of pulse pressure. The microcontroller 38 then causes the solenoid pump 30 to selectively withdraw a small fluid volume from the bladder 22 during systole (as indicated by EKG or pulse oximetry data) and reinfuses this same volume back into the bladder 22 during diastole. It is recalled that the intracranial pulse pressure is the arithmetic difference between the peak pressure at systole and the lowest pressure during diastole. Withdrawal of fluid from bladder 22 during systole will reduce the peak intracranial pressure during systole, thereby reducing PP. In addition, re-infusing the fluid during diastole will increase the intracranial diastolic pressure, also reducing PP. In other words, both actions independently and cumulatively reduce intracranial PP.

If the clinical situation were to require therapeutic augmentation of the intracranial PP such as to increase cerebral blood flow (CBF), for instance, PP modulation would withdraw fluid from the bladder 22 during diastole, thereby lowering the diastolic pressure, and reinfuse this same volume of fluid back into the bladder 22 during systole, thereby raising the systolic pressure. The cumulative effect would be to increase the intracranial PP. In both cases, the infusion/withdrawal rates and volumes of fluid moved into or out of the bladder 22 by the solenoid pump 30 are determined and controlled by microcontroller 38.

Figure 22:
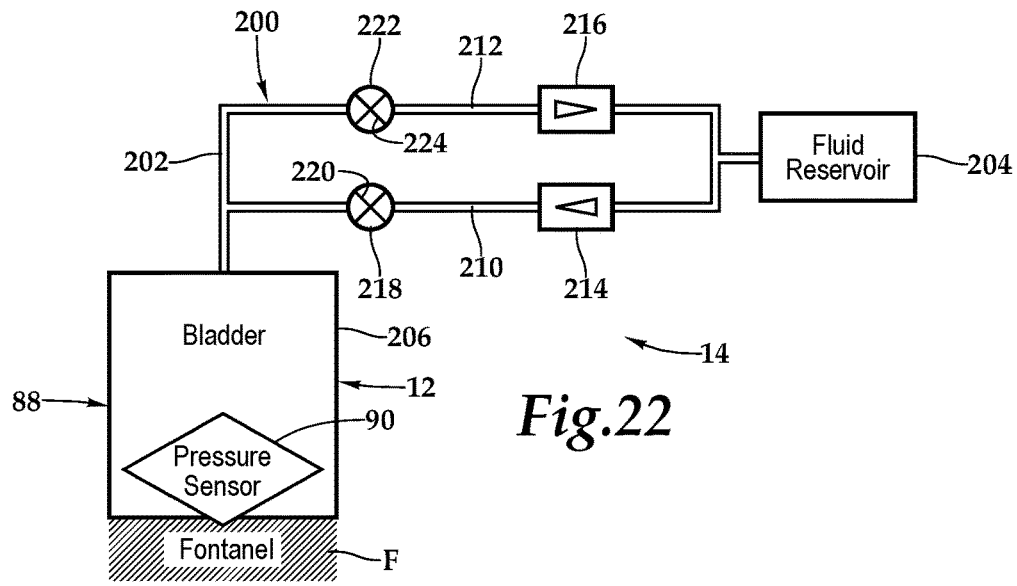
FIG. 22 is a fluid power schematic diagram depicting of another embodiment of portions of a pressure regulator and the compartment, both of which form components of the apparatus.

FIG. 22 depicts one embodiment of the compartment and the pressure regulator 14 in further detail in a hydraulic actuation application. The pressure regulator 14 may include a dual-pump arrangement 200 having conduit 202 between a fluid reservoir 204 and the pressure applicator 88, which in one embodiment, may be a bladder 22 and a pressure sensor 208. In one implementation, the pressure regulator 14 includes an infusion fluid path 210 configured to permit introduction of fluid from the fluid reservoir 204 to the pressure applicator 88, which is depicted as the bladder 22. A drain fluid path 212 is configured to permit introduction of fluid from the pressure applicator 88 to the fluid reservoir 204. It should be appreciated that the infusion fluid path 210 and the drain fluid path 212 may at least partially overlap. An infusion pump 214 is disposed within the conduit 202 to permit urging of fluid on the infusion fluid path 210 from the fluid reservoir 204 to the pressure applicator 88. Similarly, a drain pump 216 is disposed within the conduit 202 to permit urging of fluid on the drain fluid path 212 from the pressure applicator 88 to the fluid reservoir 204. A valve 218 is disposed in association with the infusion fluid path 210 with a valve element 220 that selectively, under the control of the controller 16, resists fluid flow along the infusion fluid path 210. Correspondingly, a valve 218 is disposed in association with the drain fluid path 212 with a valve element 220 that selectively, under the control of the controller 16, resists fluid flow along the drain fluid path 212.

As previously discussed, the compartment 12 includes a pressure applicator 88, shown as the bladder 22, fluidly coupled to the fluid reservoir 204 under the control of the pressure regulator 14. The pressure applicator 88 is configured to selectively apply an external pressure to the fontanel F. Further, as shown, the compartment 12 includes the pressure sensor 208 configured to measure pressure at the fontanel F. In one embodiment, the pressure sensor 208 may include a displacement sensor that measures displacement of the bladder 22. As previously alluded, the pressure sensor 208 may include, however, a sensor belonging to displacement sensors, piezoresistive sensors, capacitive sensors, piezoelectric sensors, ultrasonic sensors, or optical sensors, for example. In hydraulic actuation applications, it should be appreciated that the number and types of valves may vary as well as the number and types of pumps, and reservoir style and placement, among other hydraulic factors.

Figure 23:
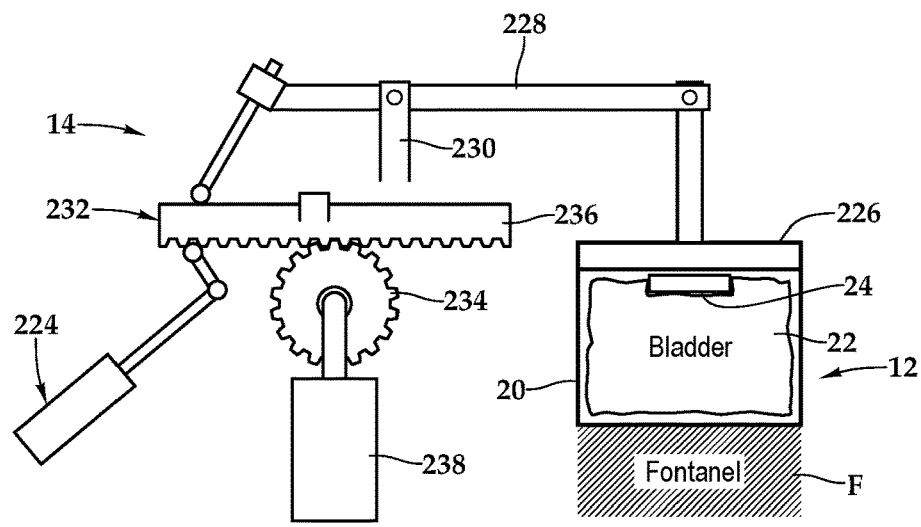
FIG. 23 is a mechanical power schematic diagram depicting of a further embodiment of portions of a pressure regulator and the compartment, both of which form components of the apparatus.

FIG. 23 depicts a further embodiment of the compartment 12 and the pressure regulator 14 in further detail, wherein a different approach is taken in order to adjust the fluid volume within the bladder 22 of the central compartment. This embodiment does not utilize a pump system to infuse or withdraw fluid into or out of the bladder of the central compartment. Instead, the bladder 22 is deformed by mechanical actuation with the movements of a micro-linear actuator 224 and a plunger 226 that directly compress the bladder 22 within the closed space of the central compartment 20 to effect a bulging (or relaxation) of the bladder wall against the scalp of the fontanel. Reduced wattage requirements of the mechanical system may prove superior to the pump system.

As shown, to achieve economy of space, the plunger 226 can serve as the ceiling of the central compartment 20. The linear actuator 224 actively displaces the plunger 226 downward, utilizing a lever 228, fulcrum 230, concentric crank slider linkages 232, and gear 234 to compress the bladder 22; decompression occurs with the spring recovery movement of the linear actuator 224. The displacement volume can be adjusted by moving the fulcrum 230 either closer to or farther away from the plunger 226. Moving the fulcrum 226 forward would result in less compression of the central compartment bladder 226 with activation of the linear actuator 224. Positioning of the fulcrum 230 is achieved with the gear 234, a miniature rack and pinion 236, a stepper motor 238, and the controller 16. In this mechanical system, the disk pressure transducer 24 is located between the bladder 22 and the plunger 226 or the central compartment 22.

In contrast to the pump/valve arrangement to modulate intracranial pulsations, the embodiment of FIG. 23 utilizes mechanical deformation of the bladder 22 in order to alter the pulsatile changes of intracranial pressure with systole and diastole. A further alternative embodiment of the mechanical deformation approach is a micro-electric motor and a gear box in the place of the linear activator.

Moreover, these embodiments that mechanically deform the bladder 22 positioned over the fontanel F require only a small reservoir adjacent to the central compartment 20. A disc plunger may be positioned just beneath the ceiling of the adjacent accessory reservoir, and this can be lowered or raised with a threaded bolt and knob to displace fluid from the accessory reservoir through tubing leading to the bladder within the central compartment 20. It is envisioned that at the time of manufacture, both bladders and any intervening tubing be fully filled with fluid that cannot traverse the walls of the bladders. In use, the care provider first reviews recorded pressure tracings. A distinct waveform indicates that the fluid volume appropriately fills the confines of the system, and the measured pressure is a good estimate of intracranial pressure. If there is no waveform, the care provider can lower the plunger within the accessory reservoir until a waveform is appreciated. If required, both bladders and connecting tubing can be removed and replaced through access in the device floor. In addition, ports to the bladder of the accessory reservoir would allow the addition of fluid, if it were ever required.

Figure 24:
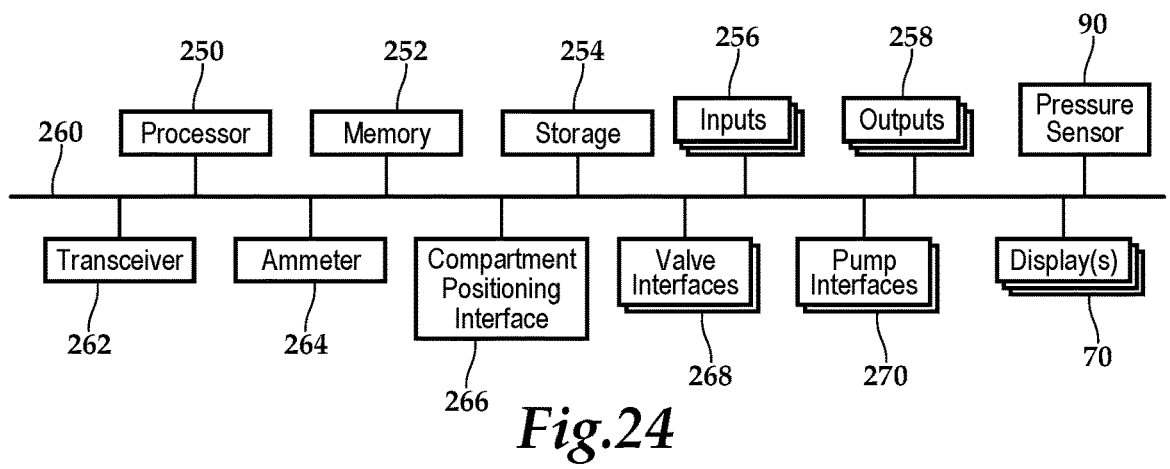
FIG. 24 is a functional block diagram depicting one embodiment of a controller, which forms a component of the apparatus.

Referring now to FIG. 24, within the housing 20, the controller 16, which may be the microcontroller 38, includes a processor 250, memory 252, storage 254, inputs 256, and outputs 258 that are interconnected by a bus architecture 260 within a mounting architecture. The processor 250 may process instructions for execution within the computing device, including instructions stored in the memory 252 or in storage 254. The memory 252 stores information within the computing device. In one implementation, the memory 252 is a volatile memory unit or units. In another implementation, the memory 252 is a non-volatile memory unit or units. Storage 254 provides capacity that is capable of providing mass storage for the computing device. Various inputs 256 and outputs 258 provide connections to and from the computing device, wherein the inputs 256 are the signals or data received by the apparatus 10, and the outputs 258 are the signals or data sent from the apparatus 10.

As previously mentioned, a pressure sensor 90 measures pressure within the central compartment 20, which will approximate ICP when the bladder 22 is inflated enough to record clear pressure waveforms. A transceiver 262 is associated with the apparatus 10 and communicatively disposed with the bus 260. The transceiver 262 may be internal, external, or a combination thereof to the housing 50. Further, the transceiver 262 may be a transmitter/receiver, receiver, or an antenna for example. Communication between various devices in a hospital room, for example, and the apparatus 10 may be enabled by a variety of wireless methodologies employed by the transceiver 262, including 802.11, 3G, 4G, Edge, WiFi, ZigBee, near field communications (NFC), infrared (IR), Bluetooth low energy and Bluetooth, for example. The controller 16 communicates with an ammeter 264, EKG interface, oxygen saturation interface, passive positioning detection signals from multiple capacitance position sensors, alarm interface indicating the device has moved, valve interfaces 268, solenoid pump interfaces 270, and displays 70. The ammeter 264 receives low voltage current applied to the metal foil on the inferior edges of each of the vertical sliders 160, 162, 164, 166 that are lowered down to touch the scalp. Skin contact will markedly change the conductance, indicating that the vertical sliders are in appropriate position. In response, the controller 16 will turn on the green (or other color) bulbs on the upper plate 106. The compartment positioning interface 266, which may include multiple capacitance position monitoring capability, will allow the care provider to align the apparatus 10 on the cranial sutures, and then monitor this baseline alignment in order to trigger a nursing alarm if the device 10 is dislodged. The valve interfaces 268 interface with valves 34, 36, for example. These latter interfaces will open or close valve 34, connecting the solenoid pump 30 to the bladder 22 while the valve 36 connecting the solenoid pump 30 to the fluid reservoir 26 is reciprocally adjusted to be open whenever valve 36 is closed and vice versa.

The memory 252 and the storage 254 are accessible to the processor 250 and include processor-executable instructions that, when executed, cause the processor 250 to execute a series of operations. In one embodiment, the processor-executable instructions cause the processor 250 to send a first control signal to the solenoid pump 30 to control the amount of fluid in the inflatable bladder 22. The first control signal may include signalization intended for the solenoid pump 30, the valves 34 and 36, or any combination thereof, by way of valve interfaces 268 and the pump interfaces 270. The processor-executable instructions may also cause the processor 250 to receive data relative to the pressure sensor 90, such as, for example, the recording of pulsatile pressure with a clear waveform from the inflatable bladder 22, thereby indicating pressure recordings reasonably approximate ICP. In response to the evaluation, the processor-executable instructions may also cause the processor 250 to send a second control signal to the solenoid pump 30 and valves 34 and 36 to stop all infusions or withdrawals of fluid so that ICP and PP can be recorded for a designated period of time; or the processor 250 may respond to instructions by the care provider to begin PP modulation in order to decrease or increase the intracranial PP by a percentage designated by the care provider.

In some embodiments, the processor-executable instructions cause the processor 250 to receive data relative to intracranial pulse pressure at the fontanel F from the pressure sensor 90 and evaluate the data to determine intracranial pulse pressure and required pulse pressure modulation, if any. The processor-executable instructions may then cause the processor to pulse pressure modulate. In one implementation, pulse pressure modulation may be achieved by the selectively withdraw of the pressure applicator from the fontanel during systole, and selectively extend the pressure applicator to the fontanel during diastole.

Figure 25:
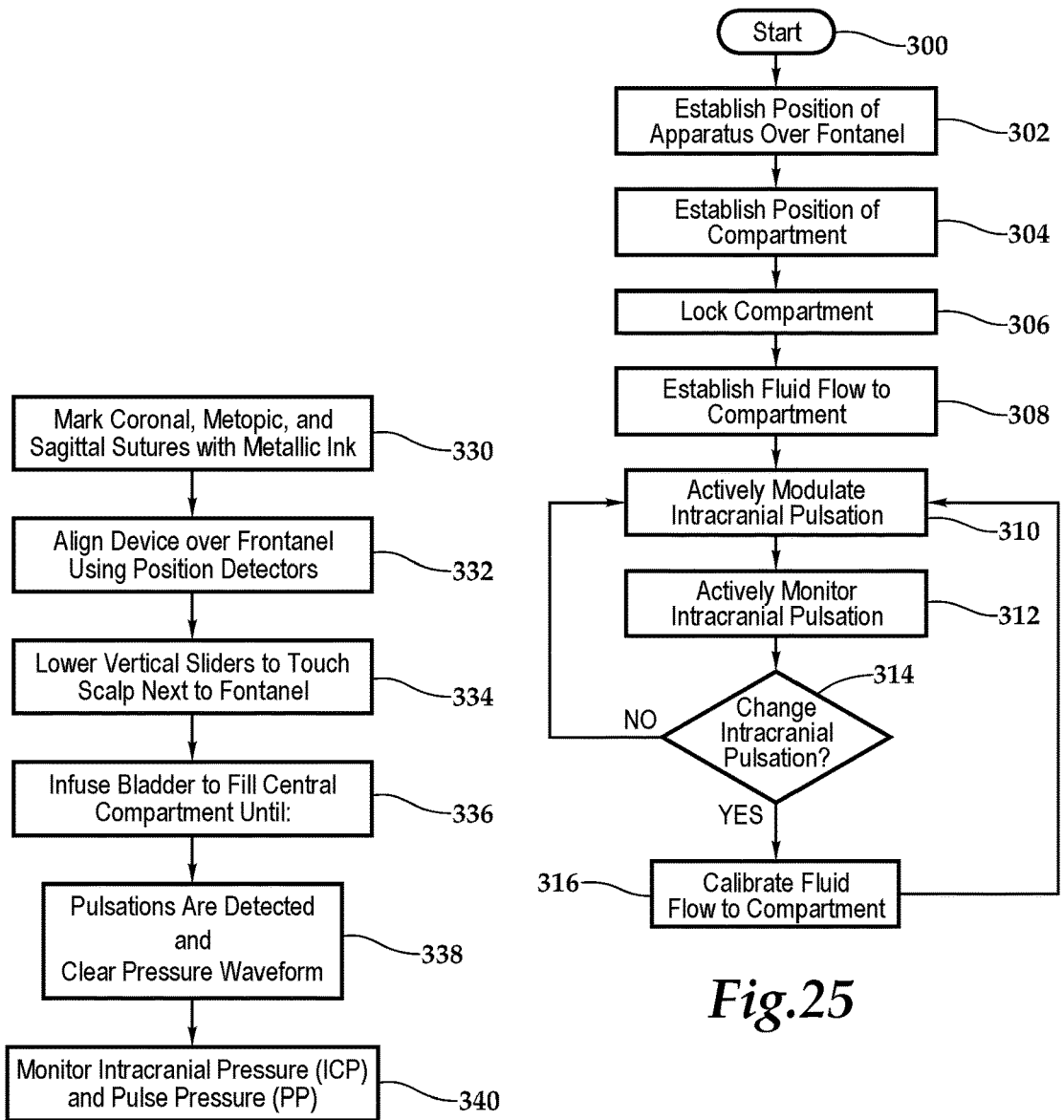
FIG. 25 is a flow chart diagram depicting one embodiment of a method for the minimally-invasive, including non-invasive, prevention and treatment of hydrocephalus in premature infants, term infants, and other individuals, according to the teachings presented herein.

Referring now to FIG. 25, one embodiment is depicted of a method for use of the apparatus for the minimally-invasive, including non-invasive, treatment of hydrocephalus. At block 300, the methodology begins. At block 302, the position of the apparatus over the fontanel is established. At block 304, the position of the compartment is established and then locked at block 306. At block 308, fluid flow to the compartment is established before actively modulating the intracranial pulsation at block 310. At block 312, the intracranial pulsation and PP is actively monitored. At decision block 314, if no change in the intracranial pulsation is desired, then the methodology returns to block 310. On the other hand, if a change in the intracranial pulsation is desired, then at block 316 the fluid flow to the compartment is calibrated before the methodology returns to block 310.

Figure 26:
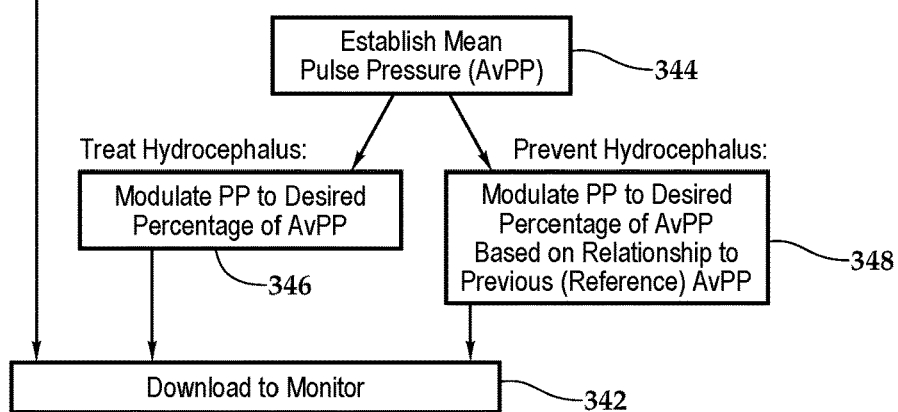
FIG. 26 is a flow chart diagram depicting another embodiment of a method for the minimally, invasive, including non-invasive, measurement of ICP and modulation of intracranial PP as a prevention and treatment of hydrocephalus in premature infants, term infants, and other individuals, according to the teachings presented herein.

Referring now to FIG. 26, one embodiment is depicted of a method for use of the apparatus for the minimally-invasive, including non-invasive, monitoring and/or treatment of hydrocephalus. At block 330, the care provider marks the metopic, sagittal, and both coronal sutures with metallic ink. At block 332, the position of the apparatus over the fontanel is established to the microcontroller as baseline. At block 334, the vertical sliders are lowered by the care provider to contact the scalp, as indicated by four green lights. At block 336, the bladder is infused with fluid to fill the central compartment and expand gently against the skin over the fontanel until pulsations with clear waveforms are detected (block 338). At block 340, ICP and intracranial PP are monitored by the apparatus. At block 342, the PP data may be downloaded to a monitor. At block 344, a mean pulse pressure value (AvPP) is determined over a designated period of time. At block 346, the microcontroller 38 actively regulates the solenoid pump to modulate intracranial PP in order to reduce (or increase, if clinically indicated) PP by a designated percentage of the present PP (AvPP) as determined by the care provider. At block 342, these modulated PP data are downloaded to a monitor. At block 348, the methodology to modulate intracranial PP in premature babies who have had IVH in order to prevent the development of post-hemorrhagic hydrocephalus may be somewhat different than what has just been suggested, and this is summarized in FIG. 27.

Figure 27:
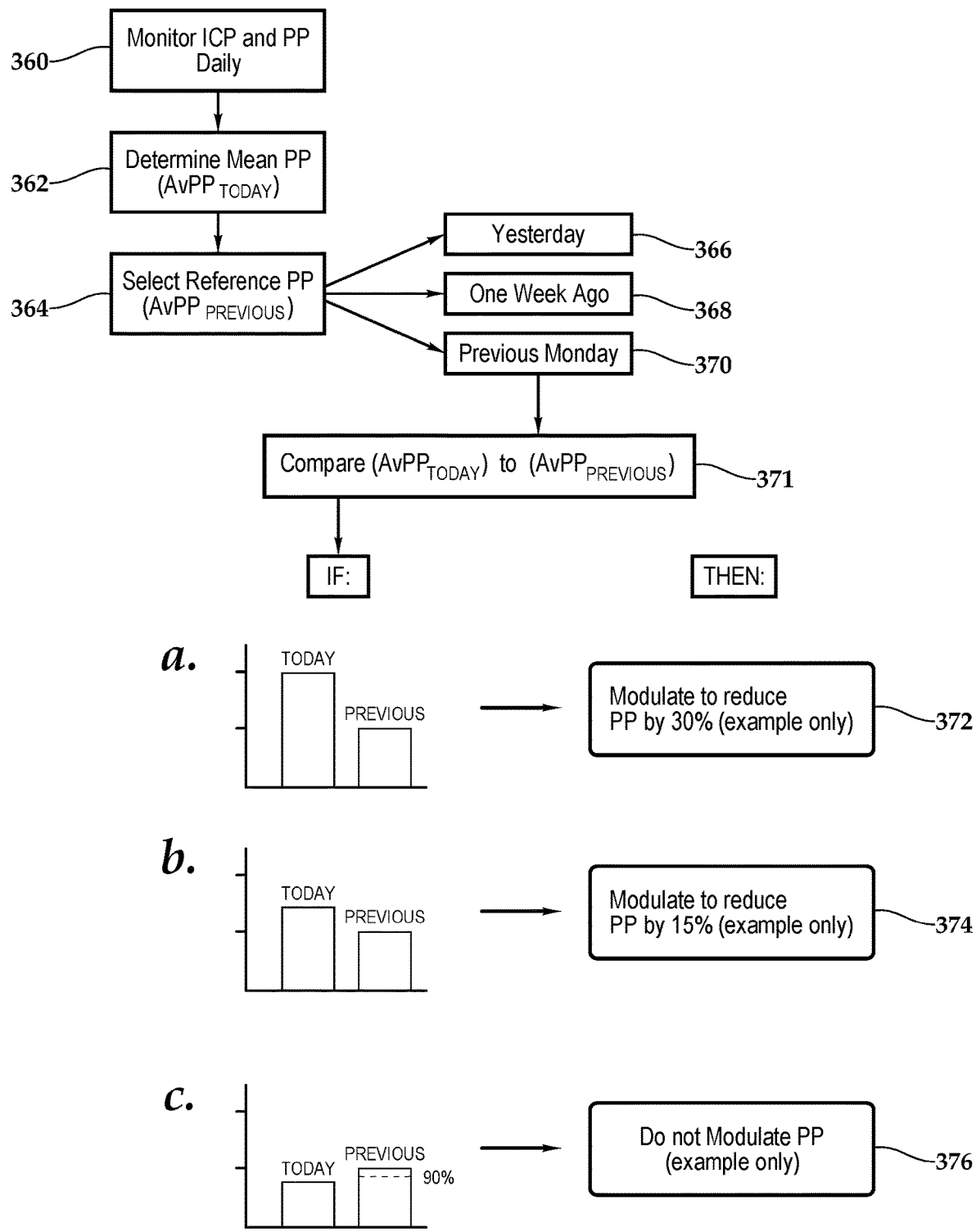
FIG. 27 is a flow chart diagram depicting one operational embodiment of a method for the minimally, invasive, including non-invasive, measurement of ICP and modulation of intracranial PP as a prevention and treatment of hydrocephalus in premature infants, term infants, and other individuals, according to the teachings presented herein.

Referring now to FIG. 27, in one embodiment of a clinical situation, at block 360, the ICP and PP may be monitored daily for a designated period of time, for example, 30 minutes. At block 362, the microcontroller determines a mean PP, called $AvPP_{TODAY}$. At block 364, the microcontroller compares $AvPP_{TODAY}$ to the last determination of mean PP, called $AvPP_{PREVIOUS}$. The care provider may instruct the microcontroller that $AvPP_{PREVIOUS}$ refers to yesterday (block 366), one week ago (block 368), or, for example, every Monday (block 370), etc. Because it is expected that abnormal increases in PP will be observed with the development of hydrocephalus, at block 371, a sliding scale of PP modulation responses can be established by the care provider, as shown in the following example, illustrated in blocks 372, 374, and 376 and summarized below.

At block 372, for $AvPP_{TODAY} \geq 2 [AvPP_{PREVIOUS}]$, modulate mean PP by reducing $AvPP_{TODAY}$ by some percentage (30% for example), set by the care provider. At block 374, for $AvPP_{TODAY} < 2 [AvPP_{PREVIOUS}]$ but $>0.9 [AvPP_{PREVIOUS}]$, modulate mean PP by reducing $AvPP_{TODAY}$ some percentage (15% for example), set by the care provider. At block 376, for $AvPP_{TODAY} < 0.9 [AvPP_{PREVIOUS}]$, do not modulate mean PP.

In another embodiment, the PP modulation sequence can gradually reduce the modulation effect over a designated time period, ultimately withdrawing all active influences on PP. In such a hydrocephalic patient, who has responded to PP modulation with improvement in the hydrocephalic ventriculomegaly, gradually weaning of the degree of PP reductions while monitoring ICP and PP can serve as a functional test to determine whether or not the hydrocephalic process has arrested. As an example, if the treatment of hydrocephalus in a particular patient were to reduce $AvPP_{TODAY}$ by 30%, the "wean sequence" might be the following:

a 25% reduction for one week,
a 20% reduction for the second week,
a 15% reduction for the third week,
a 10% reduction for the fourth week,
a 5% reduction for the fifth week, and
no reduction thereafter, but continued ICP and PP monitoring. If the patient shows no ICP or PP abnormalities and ventricular size remains stable, it would be reasonable to assume that the child indeed has arrested hydrocephalus.

The order of execution or performance of the methods and procedures illustrated and described herein is not essential, unless otherwise specified. That is, elements of the methods and procedures may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. An apparatus for a minimally-invasive, including non-invasive, modulation of intracranial pressure, the apparatus comprising:
   a housing being sized for superjacent contact on a skull having a fontanel, the housing including an opening sized for the fontanel;
   the housing securing a compartment, a pressure regulator, and a controller therein;
   the controller being interconnected communicatively with each of the compartment and the pressure regulator;
   the compartment including a pressure applicator under control of the pressure regulator, the pressure applicator being configured to selectively apply an external pressure to the fontanel;
   the compartment including a pressure sensor configured to measure an intracranial pressure and an intracranial pulse pressure at the fontanel, the intracranial pulse pressure being an arithmetic difference between a peak pressure in systole and a lowest pressure in diastole;
   the controller receiving data relative to intracranial pressure and intracranial pulse pressure at the fontanel from the pressure sensor;
   the controller, if a clinical goal is at least one of to treat hydrocephalus and prevent hydrocephalus, selectively withdrawing the pressure applicator from the fontanel during systole and selectively extending the pressure applicator to the fontanel during diastole; and
   the controller, if the clinical goal is to increase cerebral blood flow, selectively extending the pressure applicator to the fontanel during systole and selectively withdrawing the pressure applicator from the fontanel during diastole.

2. The apparatus as recited in claim 1, wherein the controller evaluates data to determine intracranial pulse pressure and required pulse pressure modulation.

3. The apparatus as recited in claim 1, wherein the pressure applicator further comprises a bladder fluidly filled.

4. The apparatus as recited in claim 3, wherein the bladder is selectively displaceable by hydraulic actuation.

5. The apparatus as recited in claim 3, wherein the bladder is selectively displaceable by mechanical actuation.

6. The apparatus as recited in claim 3, wherein the pressure sensor further comprises a disk pressure transducer that measures pressure within the bladder.

7. The apparatus as recited in claim 1, wherein the pressure sensor further comprises a sensor selected from the group consisting of displacement sensors, piezoresistive sensors, capacitive sensors, piezoelectric sensors, ultrasonic sensors, and optical sensors.

8. An apparatus for a minimally-invasive, including non-invasive, modulation of intracranial pressure, the apparatus comprising:
   a housing being sized for superjacent contact on a skull having a fontanel, the housing including an opening sized for the fontanel;
   the housing securing a compartment, a pressure regulator, and a controller therein;
   the controller being interconnected communicatively with each of the compartment and the pressure regulator;
   the compartment including a pressure applicator under control of the pressure regulator, the pressure applicator being configured to selectively apply an external pressure to the fontanel;
   the compartment including a pressure sensor configured to measure an intracranial pressure and an intracranial pulse pressure at the fontanel, the intracranial pulse pressure being an arithmetic difference between a peak pressure in systole and a lowest pressure in diastole;
   the controller receiving data relative to intracranial pressure and intracranial pulse pressure at the fontanel from the pressure sensor;
   the controller evaluating the data to determine intracranial pulse pressure and required pulse pressure modulation;
   the controller, responsive to evaluating the data, if a clinical goal is at least one of to treat hydrocephalus and prevent hydrocephalus, selectively withdrawing the pressure applicator from the fontanel during systole and selectively extending the pressure applicator to the fontanel during diastole; and
   the controller, responsive to evaluating the data, if the clinical goal is to increase cerebral blood flow, selectively extending the pressure applicator to the fontanel during systole and selectively withdrawing the pressure applicator from the fontanel during diastole.

9. The apparatus as recited in claim 8, wherein the pressure applicator further comprises a bladder fluidly filled.

10. The apparatus as recited in claim 9, wherein the bladder is selectively displaceable by hydraulic actuation.

11. The apparatus as recited in claim 9, wherein the bladder is selectively displaceable by mechanical actuation.

12. The apparatus as recited in claim 9, wherein the pressure sensor further comprises a disk pressure transducer that measures pressure within the bladder.

13. The apparatus as recited in claim 8, wherein the pressure sensor further comprises a sensor selected from the group consisting of displacement sensors, piezoresistive sensors, capacitive sensors, piezoelectric sensors, ultrasonic sensors, and optical sensors.

14. An apparatus for a minimally-invasive, including non-invasive, modulation of intracranial pressure, the apparatus comprising:
   a housing being sized for superjacent contact on a skull having a fontanel, the housing including an opening sized for the fontanel;
   the housing securing a compartment, a pressure regulator, and a controller therein;
   the controller being interconnected communicatively with each of the compartment and the pressure regulator;
   the compartment including a pressure applicator under control of the pressure regulator, the pressure applicator being configured to selectively apply an external pressure to the fontanel;
   the compartment including a pressure sensor configured to measure an intracranial pressure and an intracranial pulse pressure at the fontanel, the intracranial pulse pressure being an arithmetic difference between a peak pressure in systole and a lowest pressure in diastole;
   the controller receiving data relative to intracranial pressure and intracranial pulse pressure at the fontanel from the pressure sensor;
   the controller selectively withdrawing the pressure applicator from the fontanel during systole and selectively extending the pressure applicator to the fontanel during diastole.

15. The apparatus as recited in claim 14, wherein the controller evaluates the data to determine intracranial pulse pressure and required pulse pressure modulation.

16. The apparatus as recited in claim 14, wherein the pressure applicator further comprises a bladder fluidly filled.

17. The apparatus as recited in claim 16, wherein the bladder is selectively displaceable by hydraulic actuation.

18. The apparatus as recited in claim 16, wherein the bladder is selectively displaceable by mechanical actuation.

19. The apparatus as recited in claim 16, wherein the pressure sensor further comprises a disk pressure transducer that measures pressure within the bladder.

20. The apparatus as recited in claim 14, wherein the pressure sensor further comprises a sensor selected from the group consisting of displacement sensors, piezoresistive sensors, capacitive sensors, piezoelectric sensors, ultrasonic sensors, and optical sensors.

\* \* \* \* \*